(12) United States Patent
Hoying et al.

(10) Patent No.: US 11,890,396 B2
(45) Date of Patent: Feb. 6, 2024

(54) BONE GRAFT AND METHODS OF FABRICATION AND USE

(71) Applicant: Advanced Solutions Life Sciences, LLC, Louisville, KY (US)

(72) Inventors: James B. Hoying, Manchester, NH (US); Sarah Moss, Manchester, NH (US)

(73) Assignee: Advanced Solutions Life Sciences, LLC, Louisville, KY (US)

( * ) Notice: Subject to any disclaimer, the term of this patent is extended or adjusted under 35 U.S.C. 154(b) by 323 days.

(21) Appl. No.: 17/066,948

(22) Filed: Oct. 9, 2020

(65) Prior Publication Data

US 2021/0106723 A1    Apr. 15, 2021

Related U.S. Application Data

(60) Provisional application No. 62/914,053, filed on Oct. 11, 2019.

(51) Int. Cl.
*A61F 2/28* (2006.01)
*A61L 27/24* (2006.01)
(Continued)

(52) U.S. Cl.
CPC ............ *A61L 27/365* (2013.01); *A61F 2/28* (2013.01); *A61L 2/26* (2013.01); *A61L 27/24* (2013.01); *A61L 27/3625* (2013.01); *A61L 27/3834* (2013.01); *A61L 27/3847* (2013.01); *A61L 27/3895* (2013.01); *A61F 2002/2835* (2013.01); *A61F 2310/00982* (2013.01); *A61F 2310/00988* (2013.01); *A61F 2310/00994* (2013.01); *A61L 2430/02* (2013.01)

(58) Field of Classification Search
None
See application file for complete search history.

(56) References Cited

U.S. PATENT DOCUMENTS

| 6,123,731 A | 9/2000 | Boyce et al. |
|---|---|---|
| 9,066,994 B2 | 6/2015 | Scarborough |
| (Continued) | | |

FOREIGN PATENT DOCUMENTS

| EP | 1150624 B1 | 12/2004 |

OTHER PUBLICATIONS

Lu et al. (Stem Cells International Apr. 4, 2019; Article ID 5037578:11 pages) (Year: 2019).*

(Continued)

*Primary Examiner* — Ernst V Arnold
(74) *Attorney, Agent, or Firm* — Dinsmore & Shohl LLP

(57) ABSTRACT

Provided herein is a living bone graft including a biofabricated graft core including demineralized bone matrix and a carrier and a pre-vascularized shell at least partially enrobing the graft core, the pre-vascularized shell including isolated, intact adipose-derived microvessel fragments, mesenchymal stem cells, and collagen. The disclosed bone grafts include stromal cells that differentiate and microvessels that inosculate to provide a functional microvasculature, thereby approximating native bone repair as the graft matures in the patient. Also provided herein are methods of fabricating a bespoke, living, vascularized bone graft and methods of treating a segmental bone defect in a patient.

24 Claims, 7 Drawing Sheets

(51) Int. Cl.
*B33Y 80/00* (2015.01)
*A61L 27/36* (2006.01)
*A61L 27/38* (2006.01)
*A61L 2/26* (2006.01)

(56) References Cited

U.S. PATENT DOCUMENTS

| | | |
|---|---|---|
| 2007/0190101 A1 | 8/2007 | Yang et al. |
| 2007/0270844 A1 | 11/2007 | Lin et al. |
| 2008/0181431 A1 | 11/2008 | Missos |
| 2009/0149893 A1 | 6/2009 | Semler et al. |
| 2015/0054195 A1* | 2/2015 | Greyf ............... A61F 2/30942 264/250 |
| 2017/0232151 A1* | 8/2017 | Tuan ............... A61L 27/446 106/170.58 |
| 2018/0185547 A1 | 7/2018 | Grayson et al. |

OTHER PUBLICATIONS

Laschke et al. (European Cells and Materials 2012;24:266-277). (Year: 2012).*

International Search Report & Written Opinion for corresponding PCT Application No. PCT/US2020/054965 dated Feb. 17, 2021.

EP Communication pursuant to Article 94(3) EPC dated Sep. 25, 2023 pertaining to EP application No. 20873919.3 filed Apr. 6, 2022, pp. 1-7.

* cited by examiner

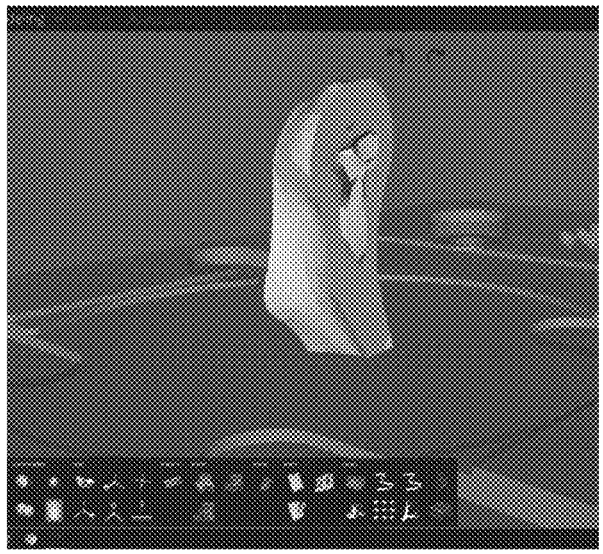 
FIG. 6A  FIG. 6B
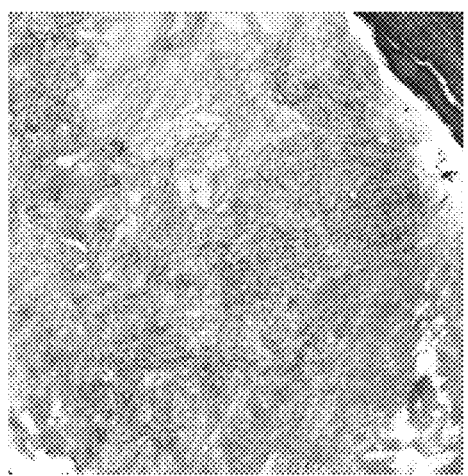 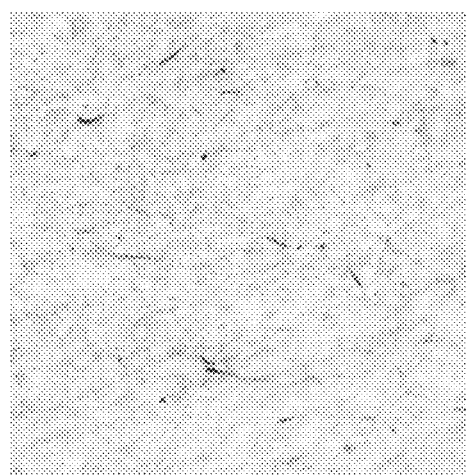
FIG. 6C  FIG. 6D

BONE GRAFT AND METHODS OF FABRICATION AND USE

CROSS-REFERENCE TO RELATED APPLICATIONS

This application claims priority to U.S. Provisional Application No. 62/914,053 filed Oct. 11, 2019, the entire contents of which are incorporated herein by reference.

TECHNICAL FIELD

The present disclosure relates to the field of bone replacements and their fabrication and use. More specifically, the present disclosure relates to bespoke, living pre-vascularized bone grafts and their methods of fabrication and use in treating bone defects.

BACKGROUND

Whether due to congenital disease, trauma, or secondary to treatment of other disease states (e.g., cancer), there is a need for bone replacements. The ideal solution is a bone graft that is vascularized, consists of native materials and components, may be customized to fit the patient's anatomy, may be customized to fit the defect geometry, and is autologous to the patient.

Current treatment modalities involve either metal or synthetic substitutes or the harvest of autologous bone grafts from other donor sites in the patient. Many bone replacement solutions involve metals (e.g., titanium) or other man-made materials that, while providing structural features similar or even superior to native bone, do not integrate well with the native bone at the implant site, cannot be revised by a surgeon for subsequent improvements (for example, to add dental appliances to a jaw bone implant), and do not change with the patient (e.g., do not grow with a pediatric patient). Also, with synthetic substitutes, it is often challenging to find an off-the-shelf solution that fits the patient and defect. Conversely, harvested autologous bone grafts must be shaped and reconfigured to fit the defect site during surgery, adding considerable time to the procedure and increasing risk to the patient. Further, additional morbidity may be associated with the donor site of the graft. A disadvantage of the current solutions is that customization of the graft shape and size is either not possible (for example, in the case of a titanium implant) or laborious and difficult (in the case of native bone grafts).

Current strategies for customization involve the use of bone particles mixed with a carrier to form a putty, or the computer numerical control (CNC) milling of cadaveric bone to a prescribed shape. With bone putties, only small defects can be repaired and such repairs involve packing the putty into the defect. Such putties cannot hold a shape independent of filling a void created by the defect. The milling of cadaveric bone offers customization of shape, however the milling process is laborious and expensive.

A need exists for customizable, living vascularized bone grafts for the repair of bone defects.

SUMMARY

Accordingly, provided herein are bespoke, living vascularized bone grafts and their methods of fabrication and use. The disclosed bone grafts do not include synthetic polymers or ceramic components. The disclosed bone grafts comprise a pre-bone graft core and a pre-vascularized shell coating capable of inosculation, such that once implanted in a patient, the immature pre-bone components of the graft core progress to form native bone that is vascularized via the shell component, which approximates a native periosteum. The bone grafts provided herein are amenable to modification after implantation to receive appliances such as dental implants and the like.

In one embodiment, a bone graft is provided, comprising: a biofabricated graft core comprising demineralized bone matrix and a carrier; and a pre-vascularized shell at least partially enrobing the graft core, the pre-vascularized shell comprising isolated intact microvessel fragments, mesenchymal stem cells, and collagen.

In another embodiment, a method of fabricating a bone graft is provided, the method comprising: (a) biofabricating a graft core from a pre-bone constituent comprising demineralized bone matrix and a carrier; (b) incubating the graft core in a first culture medium comprising a crosslinker for a first incubation period; (c) enrobing at least a portion of the graft core with a pre-vascularized shell constituent comprising isolated intact microvessel fragments, mesenchymal stem cells, and collagen; and (d) incubating the enrobed graft core of step (c) in a second culture medium for a second incubation period to provide a living bone graft.

In another embodiment, a method of treating a segmental bone defect in a patient is provided, the method comprising: providing a bone graft comprising a biofabricated graft core and a pre-vascularized shell at least partially enrobing the graft core, the pre-vascularized shell comprising isolated intact microvessel fragments, mesenchymal stem cells, and collagen; and placing the bone graft in a segmental bone defect region of the patient; wherein the microvessels inosculate and the bone graft progresses to native, mature bone in the patient.

These and other objects, features, embodiments, and advantages will become apparent to those of ordinary skill in the art from a reading of the following detailed description and the appended claims.

BRIEF DESCRIPTION OF THE DRAWINGS

The details of embodiments of the presently-disclosed subject matter are set forth in this document. Modifications to embodiments described in this document, and other embodiments, will be evident to those of ordinary skill in the art after a study of the information provided in this document.

FIG. 6A depicts a 3D model of a slice section of a human mandible modeled using TSIM® software from exemplary patient-specific imaging data.

FIG. 6B depicts a living bone graft configured to substantially fit the geometry of the segmental bone defect of FIG. 6A.

FIG. 6C is a microscopic image of a histology section stained with picrosirius red/fast green, indicating structured collagen as a precursor to bone formation in a construct comprising DBM.

FIG. 6D is a microscopic image of a histology section stained with picrosirius red/fast green, indicating structured collagen as a precursor to bone formation in a construct comprising DBM.

DESCRIPTION

Figures 1A, 1B:
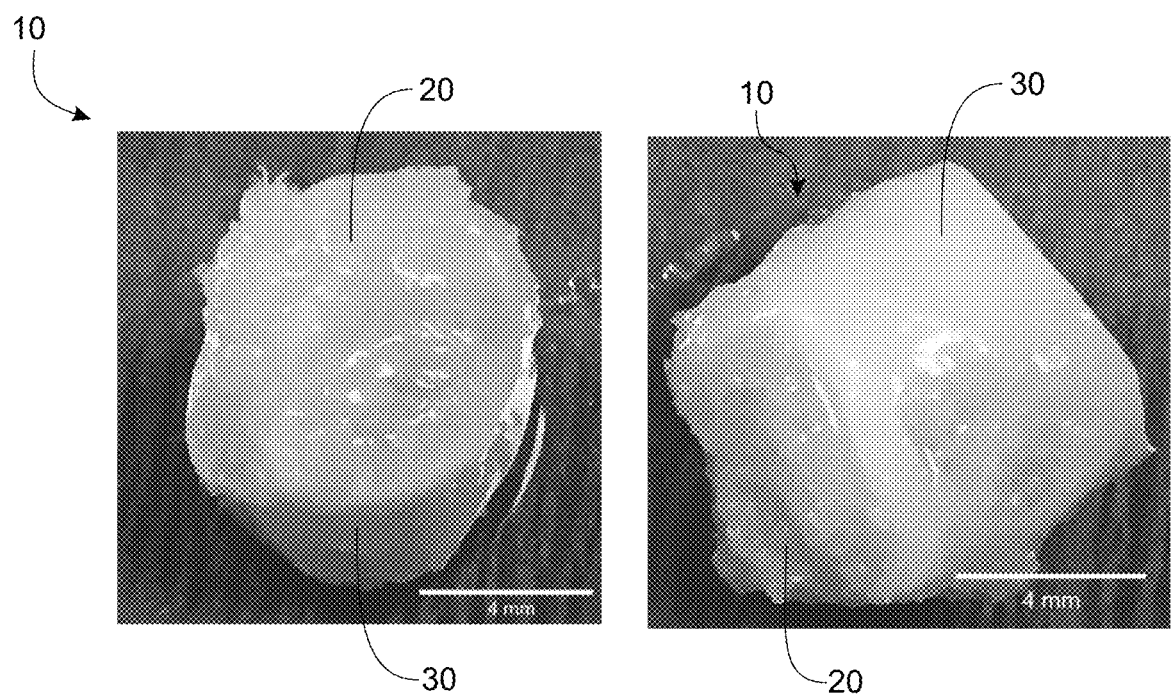
FIG. 1A is an image showing a top view of an embodiment of a bone graft according to the present disclosure.
FIG. 1B is an image showing a side view of an embodiment of a bone graft according to the present disclosure.

The details of one or more embodiments of the presently-disclosed subject matter are set forth in this document. Modifications to embodiments described in this document, and other embodiments, will be evident to those of ordinary skill in the art after a study of the information provided in this document.

While the following terms are believed to be well understood in the art, definitions are set forth to facilitate explanation of the presently-disclosed subject matter. Unless defined otherwise, all technical and scientific terms used herein have the same meaning as commonly understood by one of ordinary skill in the art to which the presently-disclosed subject matter belongs.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used in this specification and the appended claims, the singular forms "a," "an" and "the" include plural references unless the content clearly dictates otherwise.

As used herein, the term "patient" refers to any mammalian subject, including humans, non-human primates, pigs, dogs, rats, mice, and the like. In a specific embodiment, the patient is a human patient.

"Biofabricated," as used herein, refers to the automated generation of biologically functional products, for example through bioprinting or bioassembly. In embodiments, biofabrication comprises three dimensional (3D) printing, or more specifically, 3D bioprinting. Various systems for 3D printing design and fabrication are available in the art and suitable for use. In embodiments, the disclosed bone grafts are biofabricated using the BioAssemblyBot® (Advanced Solutions, Louisville, KY) and TSIM® software (Advanced Solutions, Louisville, KY) or an equivalent 3D modeling/printing software package. Advantageously, biofabrication is an agile process that reduces costs (e.g., compared to milling) and accelerates fabrication steps.

"Pre-bone," as used herein, refers to a construct or constituent as disclosed herein comprising immature bone components (e.g., mesenchymal stem cells, demineralized bone matrix, etc.) capable of developing into mature bone, for example, through cell differentiation, mineralization, bony callus formation, and progression to mature bone under suitable maturation conditions.

"Pre-vascularized," as used herein, refers to a construct or constituent comprising isolated, intact, living microvessel fragments. In embodiments, such living microvessel fragments are capable of inosculation, or sprouting, for example, under appropriate expansion conditions. In embodiments, "pre-vascularized" refers to a construct or constituent comprising living microvessel fragments that have initiated inosculation to form a putative microvasculature. The bone grafts disclosed herein are configured such that the pre-vascularized graft progresses to a vascularized graft under microvessel expansion conditions. "Vascularized, as used herein, refers to a construct or constituent comprising living microvessel fragments that have inosculated or sprouted to form a functional microvasculature.

"Segmental bone defect" refers to a bone void that will not heal spontaneously without medical intervention to fill the void. Typically, segmental bone defects result from trauma, infection, or malignancy. Bone voids require a framework or scaffold to shape and support osteogenesis. The presently disclosed bone grafts are particularly suited for the treatment of segmental bone defects, as described herein below. However, it should be understood that the use of the presently disclosed bone grafts is not restricted to the treatment of segmental bone defects and may be suitable for use in any patient in need of bone replacement treatment, regardless of defect geometry.

Microvessels (MVs) are intact microvessel fragments or segments isolated from living tissue. In embodiments, microvessels are harvested from adipose tissue, particularly human adipose tissue. MVs are native and provide a complete source of microvascular cells, which recapitulate the native vascularization. MVs display phenotypic plasticity and dynamic adaptation under maturing conditions, via angiogenesis. In embodiments, MVs for use in the instant disclosure may be allogeneic MVs or may be autologous MVs derived from patient tissue, such as adipose tissue. In a specific embodiment, the MVs are Angiomics™ MVs (Advanced Solutions, Louisville, KY).

Demineralized bone matrix (DBM) is a native material obtained from bone that has been pulverized, de-cellularized, and de-mineralized, leaving behind a bone matrix enriched with proteins necessary for bone formation. DBM is osteoinductive (generates signals leading to bone formation), osteoconductive (creates a permissive environment for bone formation), and osteogenic (produces bone).

Fibrinogen, or factor I, is a glycoprotein complex that is converted enzymatically to fibrin, which inter alia mediates capillary formation and angiogenesis, thereby promoting vascularization.

Mesenchymal stem cells (MSCs) are stromal cells derived from various sources, such as bone marrow or adipose tissue. MSCs are native cells that may differentiate to a variety of cell types, including osteoblasts, osteocytes, chondrocytes, myocytes, and adipocytes (fat cells that give rise to marrow adipose tissue). When derived from adipose tissue, MSCs may be referred to as adipose stem cells (ASCs). In an osteoinductive environment, MSCs become osteoblasts and osteocytes, capable of creating and remodeling bone matrices. In embodiments, the MSCs suitable for use in the instant disclosure may be autologous MSCs derived from the patient. In other embodiments, the MSCs are allogeneic cells.

Collagen is the main structural protein in the extracellular matrix in the various connective tissues in the body. Depending on the degree of mineralization, collagen tissues may be rigid (e.g., bone), compliant (e.g., tendon), or have a gradient from rigid to compliant (e.g., cartilage).

Gelatin is a heterogeneous mixture of proteins derived from the acidic digestion of collagen and comprises a variety of amino acids. In embodiments, gelatin employed in the disclosed products and methods is skin gelatin, or more specifically, porcine skin gelatin. Suitable sources of porcine skin gelatin are well known in the art.

Figure 7:
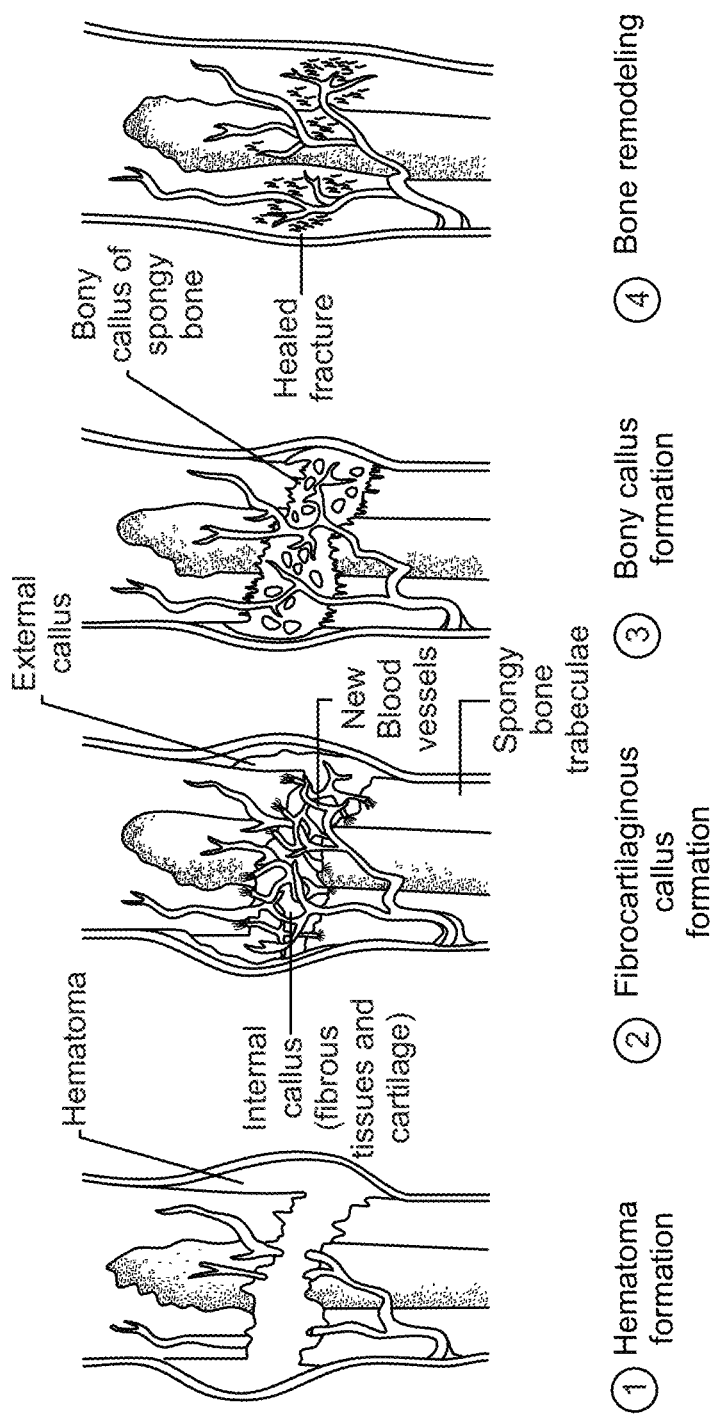
FIG. 7 is a reference illustration of the stages of native human bone repair.

The natural process of native bone repair in adults is illustrated in FIG. 7. Upon fracture, for example, a hematoma, or blood clot, forms at the site of the injury (1). Mesenchymal stem cells invade the clot and angiogenesis is initiated in the clot zone. New vessel growth originates in the periosteum, or vascularized connective tissue that surrounds the bone, as well as the bone marrow (2). MSCs are differentiated to osteogenic cells within the zone of bone repair. Provisional bone matrix (e.g., collagen) is deposited, followed by mineralization, to form the bony callus (3). The bony callus matures to repair the injured area through bone remodeling (4).

The present disclosure describes the fabrication of a bespoke living, pre-vascularized, native bone graft. Disclosed methods leverage the biology of osteogenic cells and microvessels to recapitulate native bone repair via callus formation (see FIG. 7), thereby enabling the generation of shaped bone equivalents. Components necessary for vascularized bone are configured to promote the spontaneous generation of bony constructs suitable for implantation. Final maturation and formation of bone occurs after implantation in the patient. Importantly, the process can accommodate allogeneic and/or autologous biological materials.

Living, Pre-vascularized Bone Grafts and Methods of Fabrication

Advantageously, the disclosed bone grafts comprise demineralized bone matrix, intact microvessels to enable vascularization, and only native components. The disclosed bone grafts are customizable to the patient, to the bone defect, and to the site of grafting. Bone grafts as disclosed herein comprise living materials that permit active bone remodeling, such that grafts may be further revised as needed after placement in the patient.

Referring to FIGS. 1A, 1B, fabrication of the disclosed bone grafts 10 comprises at least two components: (1) a bone graft core 20 comprising osteogenic, osteoconductive, and/or osteoinductive components, surrounded at least in part by (2) a pre-vascularized connective tissue shell 30 comprising a native microvasculature that approximates a native vascularized periosteum. The osteogenic bone graft core 20 may be generated via biofabrication methods (e.g., 3D bioprinting) to create a defined and, optionally, bespoke shape selected to match patient anatomy and defect geometry. The formulation of the core 20 enables this biofabrication approach: a precursor bone mixture comprising, in any combination, demineralized bone matrix (DBM), fibrinogen, and gelatin. Other non-cellular components such as native matrices may also be included. For subsequent evolution of the graft core into mature bone, mesenchymal stem cells (hematopoietic- or adipose-derived) may be included during fabrication of the core 20. At strategic time point(s), the core 20 is surrounded by a layer of native matrix (for example, collagen) mixed with stromal cells and isolated adipose-derived microvessels. This pre-vascularized shell 30 can be added to the core by a variety of fabrication approaches, such as 3D bioprinting. Culturing of both the core 20 and the core enrobed with the pre-vascularized shell 10 involve defined media and conditions, as described herein below. Embodiments of the biofabrication process and components are provided herein.

In one embodiment, a bone graft is provided, the bone graft comprising: a biofabricated graft core; and a pre-vascularized connective tissue shell at least partially enrobing the graft core, the pre-vascularized shell comprising isolated intact microvessel fragments.

The graft core is formed from a pre-bone constituent comprising demineralized bone matrix (DBM) and a carrier. In embodiments, the carrier comprises fibrinogen and gelatin (e.g., skin gelatin). Concentrations of DBM and carrier component(s) may vary, based on the construct to be fabricated and the selected reagents and conditions. In embodiments, concentration of DBM in the pre-bone constituent may range from 0.3 ml to 15 ml of DBM particles per ml of total volume of the remaining pre-bone constituent components. In embodiments, concentration of fibrinogen in the pre bone constituent may range from 0.01 mg/ml to 100 mg/ml. In embodiments, concentration of gelatin may range from 1% w/v to 20% w/v.

Optionally, the pre-bone constituent may further comprise additional native components, such as mesenchymal stem cells (MSCs) and/or ASCs and/or fibronectin. MSCs may be obtained from a variety of sources, such as bone marrow or adipose tissue and may be autologous or allogeneic. Concentrations of MSCs may vary from 100,000 MSC/ml to 1,000,000 MSC/ml. In embodiments, the concentration of MSCs included in the pre-bone constituent is about 500,000 MSC/ml. Concentrations of ASCs may vary from 100,000 cells/ml to 1,000,000 cells/ml. In embodiments, the concentration of ASCs included in the pre-bone constituent is about 500,000 cells/ml. Concentrations of fibronectin may vary from 0 mg/ml to 1 mg/ml. In embodiments, the concentration of fibronectin included in the pre-bone constituent is about 10 µg/ml.

In embodiments, the bone grafts disclosed herein comprise only materials native to mammals, such as humans or other mammals, and are substantially free of synthetic, man-made materials such as polymers or ceramics. In embodiments, the bone grafts provided herein are optionally substantially free of exogenous growth factors.

In embodiments, the pre-vascularized shell is formed from a pre-vascularized shell constituent comprising microvessels (MVs) and, optionally, mesenchymal stem cells and/or adipose stem cells, and, optionally, collagen. In embodiments, microvessels are isolated, intact microvessel segments or fragments obtained from human adipose tissue. Suitable MVs for use in the instant methods and grafts include Angiomics™ MVs (Advanced Solutions, Louisville, KY). Concentrations of MVs may vary from 80,000 MV/ml to 500,000 MV/ml. In embodiments, the concentration of MVs included in the pre-vascularized constituent is about 200,000 MV/ml. Concentrations of MSCs and/or ASCs may vary from 50,000 cells/ml to 2,000,000 cells/ml. In embodiments, the concentration of MSCs and/or ASCs included in the pre-vascularized shell constituent is about 200,000 MSC/ml.

Optionally, the bone graft core is bespoke in design and configured to fit a defect geometry of a specific patient. In specific embodiments, the graft core may be shaped or configured based on patient-specific imaging data, such as MRI, CT scan, x-ray, or any other suitable imaging data that may be used to define a defect geometry for preparation of a bespoke bone graft.

In embodiments, the graft core is biofabricated using 3D printing technology and compatible software. For example, in embodiments the graft core is 3D printed using a multi-axis 3D printer, such as a 2-axis, 3-axis, 4-axis, 5-axis, 6-axis, or other multi-axis printer suitable for printing the desired construct shape. Suitable 3D printer platforms include, for example, the BioAssemblyBot® (Advanced Solutions, Louisville, KY) and TSIM® software (Advanced Solutions, Louisville, KY) or an equivalent 3D modeling/printing software package.

In another embodiment, a method of fabricating a bone graft is provided, the method comprising: (a) biofabricating a graft core from a pre-bone constituent comprising demineralized bone matrix and a carrier; (b) incubating the graft core in a first culture medium comprising a crosslinker for a first incubation period; (c) enrobing at least a portion of the graft core with a pre-vascularized shell constituent comprising isolated intact microvessel fragments, mesenchymal stem cells, and collagen; and (d) incubating the enrobed graft core of step (c) in a second culture medium for a second incubation period to provide a living bone graft.

In one embodiment, a bioprinting platform is used to bioprint the core and cast the pre-vascularized shell. Generally, the process involves mixing the DBM-based formulation, printing the core structure based on patient-specific and/or defect-specific geometries, incubating the printed structure with a crosslinking solution comprising transglutaminase and thrombin/FXIIIa to "set" the core, culturing the core to initiate the bone generation process, casting the microvessel-containing shell, and culturing to condition the graft for implantation.

Figure 3:
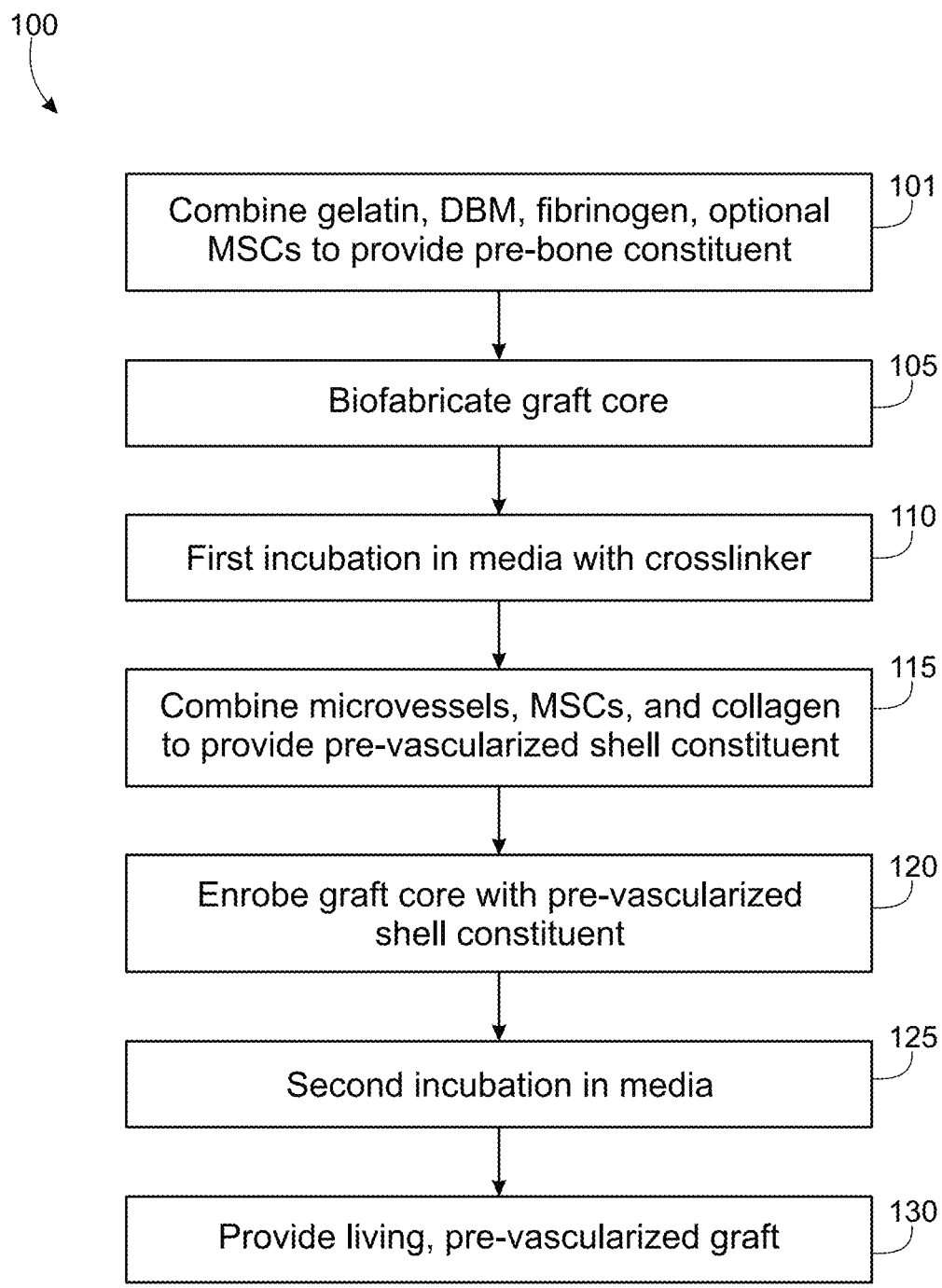
FIG. 3 is a flow chart of an embodiment of a method of fabricating a living bone graft according to the present disclosure.

Referring to FIG. 3, a flow chart is set forth describing an exemplary embodiment of a method 100 of biofabricating a bone graft according to the present disclosure. The method comprises a first step of preparing or providing a pre-bone constituent 101. In a specific embodiment, the pre-bone constituent comprises gelatin, demineralized bone matrix, fibrinogen, and optionally one or more of mesenchymal stem cells and/or ASCs and optionally fibronectin. It should be understood that the formulation of the pre-bone constituent may vary, depending on the construct to be printed and the conditions employed.

Next, the bone graft core is biofabricated 105, as described herein. Exemplary suitable methods of biofabrication 105 comprise 3D printing, for example, using a BioAssemblyBot® multi-axis 3D printer (Advanced Solutions, Louisville, KY) and TSIM® software (Advanced Solutions, Louisville, KY) or an equivalent 3D modeling/printing software package. The bone graft core may be biofabricated 105 according to patient-specific imaging data to provide a bespoke, shaped graft core.

The bone graft core is then incubated with culture medium comprising a crosslinker 110 prior to the addition of the pre-vascularized shell. Exemplary crosslinkers may be selected from thrombin, factor XIII, and transglutaminase. In another embodiment, the crosslinker comprise methacrylated gelatin. Concentrations of thrombin, factor XIII, and transglutaminase may vary, depending on the particular construct to be fabricated and the selected fabrication reagents and conditions. In embodiments, the concentration of thrombin in the crosslinking solution may range from about 0.01 U/ml to about 10 U/ml; the concentration of factor XIII may range from about 0.01 U/ml to about 10 U/ml; the concentration of transglutaminase may range from about 1 mg/ml to about 100 mg/ml. Alternatively, the concentration of methacrylated gelatin in the crosslinking solution may range from about 1% w/v to about 20% w/v.

In embodiments, the culture medium comprising a crosslinker is an RPMI 1640-based medium supplemented with B27 supplement minus vitamin A and VEGF, in addition to the transglutaminase, thrombin, and factor XIII. In embodiments, the concentration of B27 supplement minus vitamin A in the medium ranges from about 0.5× to about 2×. In embodiments, the concentration of VEGF in the medium ranges from about 0 ng/ml to about 500 ng/ml. In a specific embodiment, suitable culture medium comprising a crosslinker is formulated according to Table 1, set forth below.

The graft core is incubated in the first culture medium 110 for a first incubation period ranging from about 12 hours to about 60 days. In embodiments, the graft core is incubated with the culture medium at a temperature of 37° C. in a 5% $CO_2$ incubator. In a specific embodiment, the first incubation period is about 12 hours to about 48 hours. In a more specific embodiment, the first incubation period is about 24 hours. The first incubation period is selected to crosslink the core and adhere cells to the printed scaffold.

Still referring to FIG. 3, after the first incubation period, the pre-vascularized shell constituent is prepared or provided 115. In the exemplary method set forth in FIG. 3, the pre-vascularized shell constituent comprises intact native microvessel fragments, mesenchymal stem cells, and collagen. However, it should be understood that in other embodiments, the pre-vascularized shell constituent may comprise intact native microvessel fragments, collagen, and optionally one or more of mesenchymal stem cells and ASCs.

In embodiments, the ratio of microvessel suspension to MSC suspension is determined according to the following equation:

$$\text{Volume of Microvessel suspension} = \frac{\text{Volume of } MSC \text{ suspension}}{10}$$

Once the pre-vascularized shell constituent is prepared or provided, the bone graft core is at least partially enrobed with the pre-vascularized shell constituent 120. Such enrobing may be carried out using biofabrication tools, for example, via 3D printing, as previously described. Exemplary suitable methods of biofabrication comprise 3D printing, for example, using a BioAssemblyBot® multi-axis 3D printer (Advanced Solutions, Louisville, KY) and TSIM® software (Advanced Solutions, Louisville, KY) or an equivalent 3D modeling/printing software package.

The at least partially enrobed bone graft core is then incubated in a second culture medium for a second incubation period 125. Suitable culture medium is an RPMI 1640-based culture medium, supplemented as set forth above, but without addition of the crosslinker components. Optionally, the second culture medium further comprises an osteogenic supplement, such as StemPro Osteogenic Supplement (Fisher A1007201). In embodiments, the concentration of osteogenic supplement ranges from about a 1:1 dilution to a 1:100 dilution. In a specific embodiment, suitable culture medium is formulated according to Table 2, set forth below.

The enrobed or partially enrobed graft core is incubated in the second culture medium 125 for a second incubation period ranging from about 5 days to about 60 days or longer. In embodiments, the graft core is incubated with the second culture medium at a temperature of 37° C. in a 5% $CO_2$ incubator. In a specific embodiment, the second incubation period is approximately 14 days. The second incubation period is selected to initiate sprouting and inosculation of the microvessel fragments, thereby providing a living, pre-vascularized or vascularized bone graft 130 ready for implantation and further maturation in a patient. When osteogenic supplements are included, the second incubation period also facilitates conversion of MSCs to osteoblasts and osteocytes, thereby initiating osteogenesis and maturation of the bone graft core and expansion of the vasculature in the shell.

In a further embodiment, the enrobed or partially enrobed graft core may be incubated in a mold, such as a bespoke mold, until the implant is ready for implantation. For example, in embodiments, the enrobed or partially enrobed graft core may be placed in a flexible silicone mold configured to fit the shape of the bone graft during the second incubation period. Such a mold may optionally be 3D printed based on patient-specific imaging data. In embodiments, the bespoke graft may be packaged, transported, and/or stored in a mold until such time as the implant is ready for placement in the patient.

Methods of Use

In embodiments, a method of treating a segmental bone defect in a patient is provided, the method comprising: providing a bone graft comprising a biofabricated graft core and a pre-vascularized shell at least partially enrobing the graft core, the pre-vascularized shell comprising isolated intact microvessel fragments, mesenchymal stem cells, and collagen; and placing the bone graft in a segmental bone defect region of the patient; wherein the microvessel fragments inosculate and the bone graft progresses to native, mature bone in the patient.

In embodiments, it may be necessary to mechanically brace the bone graft at the site of the segmental defect, in order to mechanically support the construct and hold the construct in place in the patient. Such mechanical bracing may be accomplished by methods known in the art, for example, by the placement of brackets, pins, screws, plates, wires, and the like.

In embodiments, the bone graft is bespoke and configured to fit a defect geometry of a specific patient. In specific embodiments, the bone graft, or more specifically the graft core, may be shaped or configured based on patient-specific imaging data, such as MRI, CT scan, x-ray, or other suitable imaging data.

In embodiments, the graft core is biofabricated using 3D printing technology and compatible software. For example, in embodiments the graft core is 3D printed using a multi-axis 3D printer, such as a 2-axis, 3-axis, 4-axis, 5-axis, 6-axis, or other multi-axis printer suitable for printing the desired construct shape. Suitable 3D printer platforms include, for example, the BioAssemblyBot® (Advanced Solutions, Louisville, KY) and TSIM® software (Advanced Solutions, Louisville, KY) or an equivalent 3D modeling/printing software package.

FIG. 5 depicts exemplary placement of a bespoke bone graft according to an embodiment of the disclosure in a segmental bone defect region of a model human mandible. FIG. 5A depicts a model human mandible having a segmental bone defect region 50. FIG. 5B depicts a bespoke living bone graft 10 as disclosed herein, which has been biofabricated to fit the geometry of the segmental defect 50. In FIG. 5B, the bespoke bone graft 10 is shown upside down, such that the portion of the graft that contacts the interior of the mandible is oriented upward, and the portion of the graft that aligns with the patient's tooth line is oriented downward. FIGS. 5C-5D show the bespoke implant 10 positioned in the segmental defect region 50.

FIG. 6A depicts an exemplary 3D model of a segmental bone defect (here, a slice section of a human mandible) modeled using the TSIM® software platform from exemplary patient-specific imaging data. FIG. 6B depicts a 3D printed bone graft, configured to substantially fit the geometry of the segmental bone defect, as described herein. FIGS. 6C and 6D depict histology sections stained with picrosirius red and fast green indicating structured collagen as a precursor to bone formation with and without DBM, respectively.

In certain embodiments, a living bone graft may optionally be "banked" in an ectopic location or position in the body of a patient prior to placement at the site of the segmental defect. Such banking facilitates conditioning of the implant, for example, to permit the mesenchymal stem cells and/or adipose stem cells to differentiate into mature cells, and/or to permit the microvessels to further inosculate and develop a more complete capillary bed and functional microvasculature. In embodiments, the living bone graft is surgically placed under a flap of tissue at a banking site (e.g., ectopic site) of the patient's body. For example, in the case of a mandible implant, the bone graft may be banked under a tissue flap in the patient's chin for a period of time, to facilitate differentiation and maturation to a more composite implant, prior to removal and from the ectopic site and placement at the site of the bone defect. Such tissue banking promotes graft maturation and vascularization and also creates a free or leashed flap (e.g., osteomyocutaneous flap) for implantation into the defect site.

EXAMPLES

The following examples are given by way of illustration are not intended to limit the scope of the disclosure.

Example 1

Preparation of Reagents for Biofabricating the Graft Core

All reagents are sterilized before use. Proper aseptic techniques is utilized throughout the procedure.

Graft Core Pre-Bone Constituent Stock Solution Preparation

Gelatin: A 15% w/v solution of gelatin from porcine skin 300 Bloom (Sigma G1890-500G) in 1× PBS is prepared. The solution is placed on a hot plate and mixed vigorously on high heat until the gelatin has dissolved. After gelatin has dissolved, the solution is sterilely filtered through a 0.22 μm filter and placed in a 37° C. water bath to cool. Sterile gelatin stocks may be stored at 4° C. for 1 week and reheated for use. The concentration of gelatin employed in the bone graft core constituent ink may be adjusted, depending on the construct to be printed and the specific fabrication conditions.

Fibrinogen: A 60 mg/ml solution of fibrinogen from human plasma (Sigma F4883-1G) in 1× PBS is prepared. The solution is vortexed to mix then placed in a 37° C. water bath for 20 minutes to dissolve the fibrinogen. After fibrinogen is dissolved, the solution is sterilely filtered through a 0.22 μm filter. Fibrinogen solution is preferably used the same day it is prepared. The concentration of fibrinogen employed in the bone graft core constituent ink may be adjusted, depending on the construct to be printed and the fabrication conditions.

Freeze-Dried Demineralized Bone Matrix (DBM): DBM (Animal sources: veterinary transplant services; human sources: AlloSource, Cincinnati, OH; LifeLink Tissue Bank, Tampa, FL) having a particle size of 500 μm or smaller is suitable for use.

Human mesenchymal stem cells (MSCs): MSCs of passage 3 or lower (RoosterBio, Frederick, MD, MSC-003 KT-002) are suitable for use.

Fibronectin: Fibronectin from human plasma (Sigma #F1056) is dissolved in 1× PBS at a stock concentration of 1 mg/ml. Fibronectin should be aliquoted and stored at −20° C. to avoid freeze/thaw cycles.

Cell Culture Medium with Crosslinker

Thrombin: Thrombin from human plasma (Sigma #T6884-250UN) is dissolved in 1× PBS at a stock concentration of 250 U/ml. Thrombin is aliquoted and stored at −20° C. to avoid freeze/thaw cycles. The concentration of thrombin employed may be adjusted, depending on the construct to be printed and the fabrication conditions.

Factor XIII: Factor XIII (Enzyme Research Labs HFXIIIa 1314) is dissolved in 1× PBS at a stock concentration of 300-400 U/ml. Factor XIII should be aliquoted and stored at −20° C. to avoid freeze/thaw cycles. The concentration of Factor XIII employed may be adjusted, depending on the construct to be printed and the specific fabrication conditions.

Transglutaminase: A stock solution of 60 mg/ml transglutaminase (Amazon MooGloo-TI Formulation) in RPMI 1640 is prepared. The solution is vortexed to mix and then placed in a 37° C. water bath for 20 minutes to dissolve the transglutaminase. After transglutaminase is dissolved, the solution is sterilely filtered through a 20 μm filter.

VEGF: 0.1% BSA is added to UltraPure water and sterilely filtered. VEGF (Peprotech 100-20) is reconstituted in the sterile solution to a concentration of 50 μg/ml.

B27 Supplement: 50× minus Vitamin A (Fisher 12587010)

A suitable culture medium with crosslinker is formulated according to Table 1.

TABLE 1

Culture Medium with Crosslinker

| Medium Component | Final Medium Concentration |
| --- | --- |
| RPMI 1640 | |
| B27 minus vitamin A | 1X |
| Vascular Endothelial Growth Factor (VEGF) | 50 ng/ml |
| Transglutaminase | 10 mg/ml |
| Thrombin | 1 U/ml |
| Factor XIII | 1.4 U/ml |

MSC Culture Medium Preparation

MSC culture medium comprises DMEM:F12 containing 10% fetal bovine serum (FBS).

Example 2

Biofabrication of the Graft Core and Crosslinking

The amount of graft core pre-bone constituent (e.g., 3D printing ink) will vary, depending on the size of the construct to be printed. In a petri dish, fibronectin, fibrinogen, MSCs, and DBM are combined at a concentration of 10 μg/ml, 10 mg/ml, 500,000 MSC/ml, and ⅛ tsp/ml, respectively, and gently mixed.

Sterile gelatin is removed from the water bath and added to the fibronectin/fibrinogen/MSC/DBM solution for a final concentration of 7% w/v gelatin. Ensure gelatin is not warmer than 37° C. before adding to printing Ink. The completed printing ink mixture is mixed well.

The completed printing ink is transferred to a sterile printing cartridge. The cartridge is inverted while the solution is gelling to maintain suspension. After the solution has gelled, an 18GA conical needle is placed on the end of the printing cartridge. The solution is now ready to be used for 3D printing applications.

Ink can be printed using any suitable 3D system, although print settings may vary. Using pneumatic printing methods on the BioBot® Basic or BioAssemblyBot® 3D printer (Advanced Solutions, Louisville, KY), the recommended print settings are as follows: Pressure: 7-20 PSI; Speed: 5-10 mm/sec; Acceleration: 650 mm/sec^2; Start Delay: 25 msec; Line Height: 1 mm; Line Width: 0.5 mm. Construct should be printed with 2 hours of thawing MCSs to ensure cell viability.

After preparing the ink, constructs should be printed within 2 hours of thawing MCSs in order to ensure viability.

After 3D printing, the construct is submerged in the tissue culture medium containing transglutaminase crosslinker and incubated in a 37° C. 5% $CO_2$ incubator for approximately 2-24 hours.

Figure 4A:
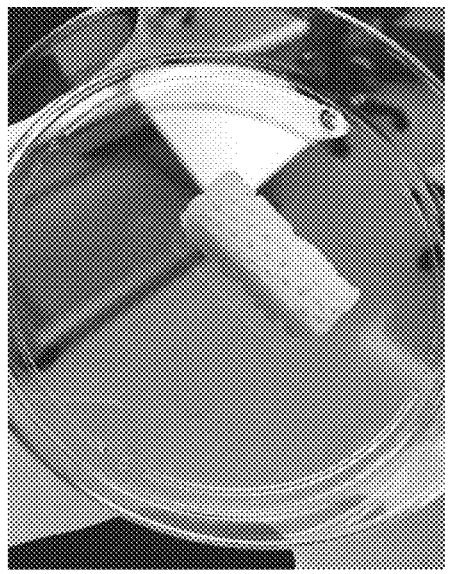
FIG. 4A is an image of a perspective view of an exemplary biofabricated graft core according to the present disclosure.
Figure 4B:
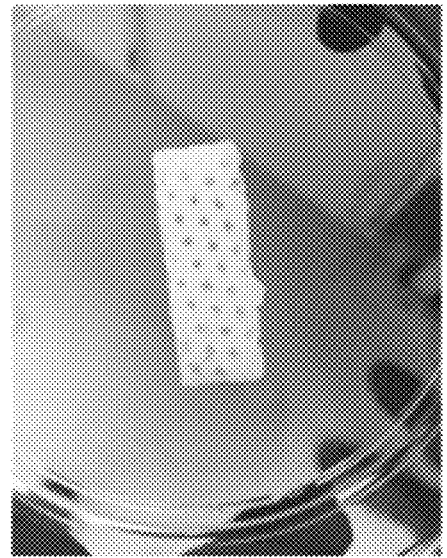
FIG. 4B is an image of a top view of an exemplary biofabricated graft core according to the present disclosure.

FIGS. 4A and 4B are images depicting a biofabricated bone graft core construct as described herein.

Example 3

Preparation of Reagents for Pre-Vascularized Shell Constituent

Approximately one day after printing, the pre-vascularized shell constituent (e.g., casting solution) is added to the printed construct. Reagents are prepared as follows:

4X DMEM: 10 g of powdered DMEM (low glucose w/phenol red; Fisher Scientific #31600-034) and 3.7 g of sodium bicarbonate (Fisher Scientific #S233-3) are added to 10 ml 1M HEPES (Lonza #17-737E). The components are mixed until dissolved and brought to a final volume of 250 ml in UltraPure water. The solution is sterilely filtered through 0.22 μm filter. 4× DMEM and may be stored at 4° C. for up to 7 days.

Collagen I: Undiluted, collagen stocks may be stored at 4° C. for up to about 6 months. Longer storage times may result in poor neovessel growth. All components of the collagen mix are kept on ice throughout the preparation. Chilling pipette tips may also help prevent collagen from gelling. Extra collagen may be prepared (for example, approximately 50% extra) to compensate for tube and pipette wall adhesion of the viscous collagen. Once prepared, the collagen solution should be used within 30 minutes.

Collagen is prepared from 4x DMEM, sterile UltraPure or MilliQ water, and high concentration stock collagen (e.g., rat tail collagen I, Corning® #354249). The volume of reagents needed to dilute stock collagen to the desired concentration is calculated as follows:

$$\text{Volume of Stock Collagen} = \frac{(\text{Desired Collagen Concentration}) * (\text{Desired Volume of Collagen})}{\text{Concentration of Stock Collagen}}$$

$$\text{Volume of } 4X \text{ } DMEM = (\text{Desired Volume of Collagen}) * (0.25)$$

$$\text{Volume of } NAOH = \text{Volume of Stock Collage} * 0.023$$

$$Vol\ DI\ \text{Water} =$$

$$\text{Desired } Vol \text{ Collagen} - (Vol\ 4X\ DMEM + Vol \text{ Stock Collagen} +$$

$$Vol\ NAOH + 50\ \mu l\ MV \text{ Suspension})$$

These equations assume 50 μl of microvessel/MSC suspension will be added to the total volume of collagen below. This may be adjusted if different volumes are used.

All the reagents are added together in a 15 ml centrifuge tube, with the collagen stock being the last reagent added. If the solution color is orange or yellow, a few microliters of sterile 1N NaOH are added, mixing well. Repeat until the mix turns red/pink (reflecting pH 7.4), waiting 1 minute between each addition. If the solution turns magenta, the solution is too basic and 1M HCl should be added back to adjust pH. Orange color indicates the solution is too acidic and additional NaOH should be added until the desired red/pink color is achieved, indicating a pH of 7.4. Importantly, NaOH or HCl should not be added once the microvessels have been added to the collagen mixture.

Thawing medium is prepared as a DMEM:F12 50:50 mixture containing 10% fetal bovine serum (FBS).

Pre-vascularized shell constituent (casting solution): The pre-vascularized shell constituent is prepared by combining the collagen stock, human adipose microvessels, and mesenchymal stem cells.

Cell culture medium with optional osteogenic supplements: 0.1% BSA is added to UltraPure water and sterilely filtered. VEGF is reconstituted with the sterile solution to a concentration of 50 μg/ml. B27, VEGF, and optional StemPro Supplement are added to RPMI to a final concentration as set forward in Table 2.

TABLE 2

Culture medium

| Medium Component | Final Medium Concentration |
| --- | --- |
| RPMI 1640 | |
| B27 minus vitamin A | 1X |
| VEGF | 50 ng/ml |
| Optional: StemPro Osteogenic Supplement (Fischer A1007201) | 1:10 dilution |

Different casting strategies are suitable for use, depending on the desired concentration of MSCs in the pre-vascularized shell. Various MSC densities will determine collagen contraction and compaction rates. Example 4 sets forth an exemplary procedure for casting the pre-vascularized shell onto a DBM bone graft core.

Example 4

Pre-Vascular Shell Addition

The total number of microvessels, MSCs, and volume of collagen/microvessel suspension required is determined. Microvessels are routinely used at a density of 200,000 microvessels/ml for robust angiogenesis. Lower microvessel density may result in slow growth and/or microvessel death.

Effective collagen concentrations range from 1.5 mg/ml to 7 mg/ml. In this embodiment, 5 mg/ml is the concentration employed. MSC concentration is about 200,000 MSCs/ml. The volume of suspension of collagen and MSCs should be sufficient to submerge the printed construct.

Microvessels are rapidly thawed in a 37° C. water bath and moved to a centrifuge tube containing approximately 10 ml of thawing medium. A micropipette and culture medium are used to rinse out the vial.

The desired number of MSCs are added to the MVs with thawing medium. The microvessel/MSC suspension is then centrifuged at 400×G for 4 minutes. Vessels/MSCs are resuspended after centrifugation directly in collagen. If multiple collagen or microvessel concentrations are contemplated, the suspension may be divided and each group may be centrifuged separately.

The MSCs are passaged, counted, and then pelleted by centrifuging at 200×G for 8 minutes.

While microvessels are in the centrifuge, the collagen gel is prepared. Undiluted, collagen stocks may be stored at 4° C. for up to about 6 months. Longer storage times may result in poor neovessel growth. All components of the collagen mix are kept on ice throughout the preparation. Chilling pipette tips may also help prevent collagen from gelling. Extra collagen may be prepared (for example, approximately 50% extra) to compensate for tube and pipette wall adhesion of the viscous collagen. Once prepared, use the collagen solution should be used within 30 minutes. Collagen is prepared as discussed in Example 3.

The supernatant is then aspirated from the microvessel/MSC pellet so that <50 μl media remain above the pellet. The microvessels are resuspended with a micropipette and the centrifuge tube is placed on ice. The tube is kept on ice for a minimum of one minute, thereby cooling the tube and preventing the collagen from gelling prematurely.

The desired volume of cold collagen solution is dispensed into the tube containing the microvessel pellet and the pellet is then resuspended with a micropipette, taking care to avoid introducing bubbles.

A well plate is placed on an ice bath and allowed to cool for at least one minute. The MSC/collagen mix is then dispensed, for example via 3D printing methods, into the well plate. Using sterile forceps, the DBM/MSC/gelatin graft core construct is carefully placed into the cold collagen/MSC bath.

Using a micropipette, multiple spots of 50 µl MV/collagen suspension is added in a radial pattern around the printed construct. Avoid tilting the plate so as to avoid moving the microvessels once they have been added.

The plate is then placed in a 37° C., 5% $CO_2$ incubator for 1 hour to gel the collagen.

Culture medium is then added to each well, at a volume equal to the volume of collagen in the well. The well plate is then incubated at 37° C. in a % $CO_2$ incubator, changing the medium every 2 days for the first week and every 4 days afterwards. More frequent medium changes may slow neovessel growth.

Neovessel sprouting is visible within 3-4 days. Contraction of the collagen begins after neovessel sprouting is initiated. Pre-vascular shell is permitted to contract to the desired tissue stiffness.

Figure 4C:
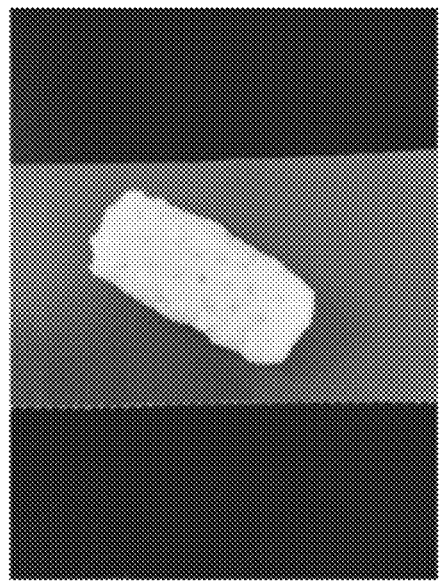
FIG. 4C is an image of a top view of an exemplary biofabricated graft core substantially enrobed with a pre-vascularized shell according to the present disclosure.
Figure 5A:
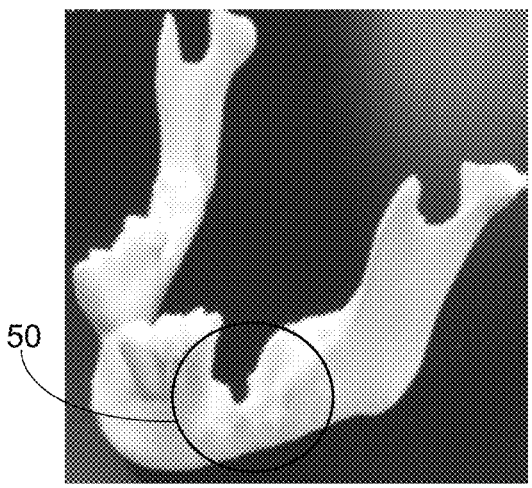
FIG. 5 depicts stages of placement of a bespoke living bone graft in a segmental bone defect region. (A) is an image depicting a model human mandible having a segmental bone defect (circled). (B) is an image depicting a bespoke living bone graft designed to fit in the segmental bone defect of FIG. 5(A). (C) and (D) are images depicting two different view of placement of the bespoke living bone graft in the segmental defect region.
Figure 5B:
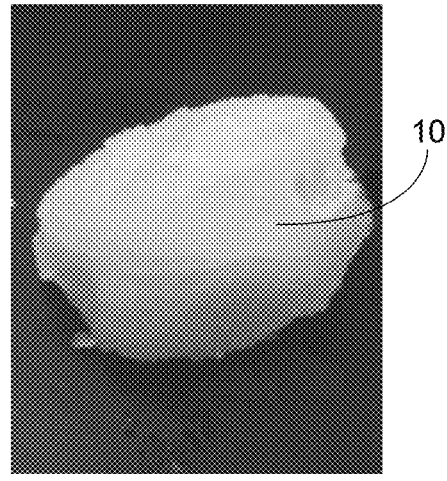
Figure 5C:
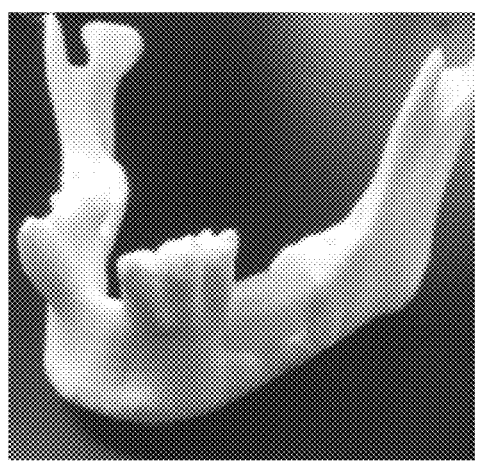
Figure 5D:
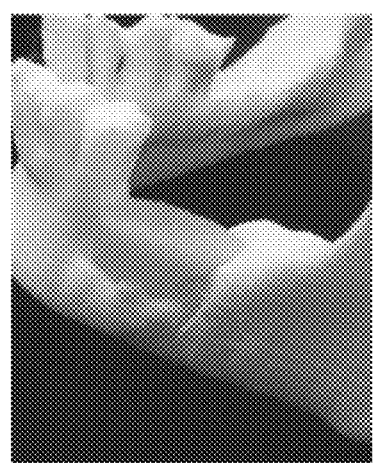

FIG. 4C is an image depicting an exemplary bone graft substantially enrobed with a pre-vascular shell, as described herein.

Example 5

Vascularization of a Living Bone Graft

Figure 2A:
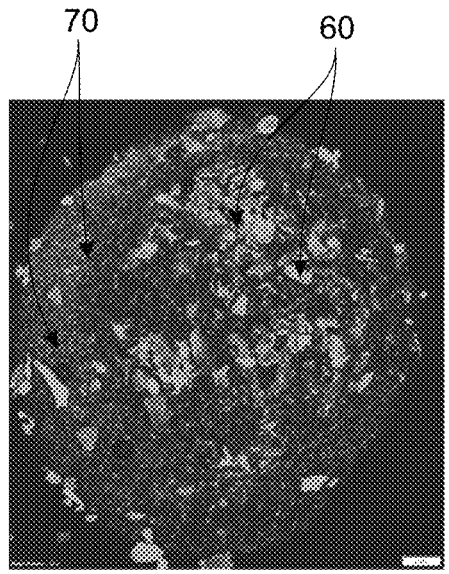
FIG. 2A is an image of an embodiment of a living bone graft according to the present disclosure stained with UEA-1 lectin, wherein demineralized bone matrix is shown in light grey and expanded microvessels are shown in dark grey.
Figure 2B:
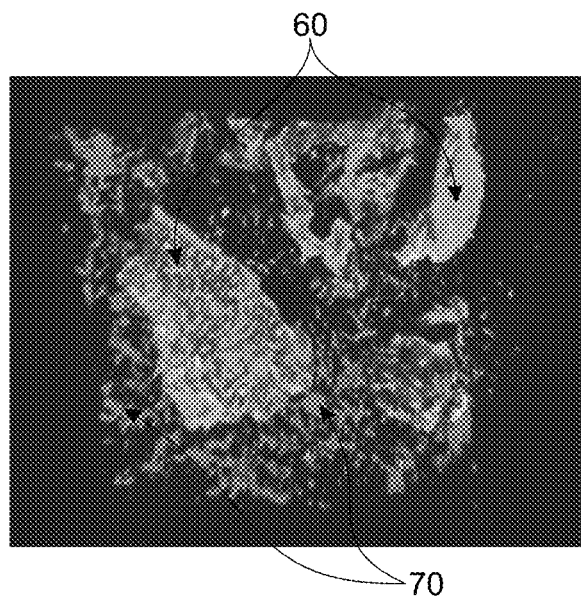
FIG. 2B is an image of an embodiment of a living bone graft according to the present disclosure stained with UEA-1 lectin, wherein demineralized bone matrix is shown in light grey and expanded microvessels are shown in dark grey.
Figure 2C:
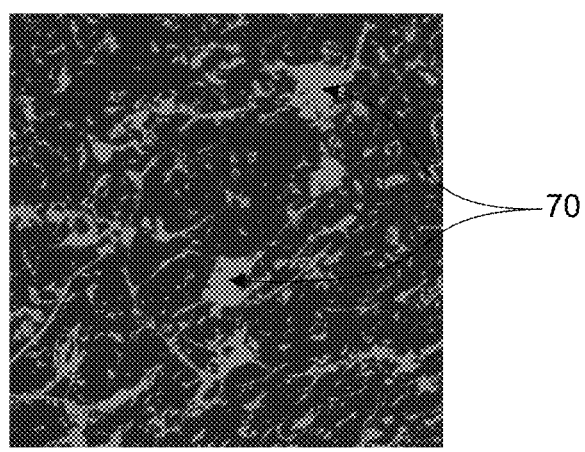
FIG. 2C is a microscopic image of expanded microvessels of an embodiment of a living bone graft according to the present disclosure stained with UEA-1 lectin.

A living, vascularized bone graft was biofabricated according to the methods disclosed herein. The construct was then stained with picrosirius red and fast green to visualize the demineralized bone matrix and the microvessels, and more particularly, the inosculating microvessels of the graft. FIGS. 2A-2C are microscopic images of the stained graft, wherein demineralized bone matrix 60 was stained green and is visualized in the images as a lighter grey shade, and wherein microvessels 70 were stained red and are visualized in the images as a darker grey shade. As shown in FIGS. 2A-2C, the bone graft comprises microvessel fragments that inosculate to provide a functioning capillary bed in the living bone graft.

All documents cited are incorporated herein by reference; the citation of any document is not to be construed as an admission that it is prior art with respect to the present invention.

It is to be further understood that where descriptions of various embodiments use the term "comprising," and/or "including" those skilled in the art would understand that in some specific instances, an embodiment can be alternatively described using language "consisting essentially of" or "consisting of."

The foregoing description is illustrative of particular embodiments of the invention but is not meant to be a limitation upon the practice thereof. While particular embodiments have been illustrated and described, it would be obvious to one skilled in the art that various other changes and modifications can be made without departing from the spirit and scope of the invention. It is therefore intended to cover in the appended claims all such changes and modifications that are within the scope of this invention.

We claim:

1. A bone graft comprising:
   a 3D printed graft core formed of a pre-bone constituent comprising demineralized bone matrix (DBM) and a carrier; and
   a pre-vascularized shell at least partially enrobing the graft core, the pre-vascularized shell formed of a pre-vascularized shell constituent comprising:
      from about 80,000 to about 500,000 microvessels/ml isolated intact microvessel fragments,
      mesenchymal stem cells, and
      from about 1.5 to about 7 mg/ml collagen.

2. The bone graft of claim 1, wherein the carrier of the pre-bone constituent comprises fibrinogen and gelatin.

3. The bone graft of claim 2, wherein the graft core further comprises one or more of mesenchymal stem cells and adipose stem cells.

4. The bone graft of claim 1, wherein the graft core is a bespoke graft core configured to fit a defect geometry of a specific patient.

5. The bone graft of claim 4, wherein the graft core is shaped based on patient-specific imaging data.

6. The bone graft of claim 1, wherein the isolated microvessel fragments are human adipose-derived whole microvessel segments.

7. The bone graft of claim 1, wherein the bone graft is not exogenously doped with growth factors.

8. A method of fabricating a bone graft, the method comprising:
   (a) biofabricating via 3D-printing a graft core from a pre-bone constituent comprising demineralized bone matrix (DBM) and a carrier;
   (b) incubating the graft core in a first culture medium comprising a crosslinker for a first incubation period;
   (c) enrobing at least a portion of the graft core with a pre-vascularized shell constituent comprising from about 80,000 to about 500,000 microvessels/ml isolated intact microvessel fragments, mesenchymal stem cells, and from about 1.5 to about 7 mg/ml collagen; and
   (d) incubating the enrobed graft core of step (c) in a second culture medium for a second incubation period to provide a living bone graft.

9. The method of claim 8, wherein the carrier comprises fibrinogen and skin gelatin.

10. The method of claim 8, wherein the pre-bone constituent further comprises one or more of mesenchymal stem cells and adipose stem cells.

11. The method of claim 8, wherein the graft core is 3D printed based on patient-specific imaging data.

12. The method of claim 8, wherein the first culture medium comprises thrombin, factor XIII, and transglutaminase.

13. The method of claim 8, wherein the first incubation period ranges from about 12 hours to about 48 hours.

14. The method of claim 8, wherein enrobing at least a portion of the graft core with the pre-vascularized shell constituent is carried out by 3D printing.

15. The method of claim 8, wherein the second culture medium comprises RPMI, B-27 supplement minus vitamin A, and vascular endothelial growth factor (VEGF).

16. The method of claim 8, wherein the second incubation period ranges from about 3 days to about 14 days.

17. The method of claim 8, wherein incubating comprises incubating at about 37° C.

18. A method of treating a segmental bone defect in a patient, the method comprising:
   providing a bone graft comprising a 3D-printed graft core formed of a pre-bone constituent comprising demineralized bone matrix (DBM) and a carrier, and a pre-vascularized shell at least partially enrobing the graft core, the pre-vascularized shell formed of a pre-vascularized shell constituent comprising from about 80,000 to about 500,000 microvessels/ml isolated intact microvessel fragments, mesenchymal stem cells, and from about 1.5 to about 7 mg/ml collagen; and placing the bone graft in a segmental bone defect region of the patient; wherein the microvessel fragments inosculate and the bone graft progresses to native, mature bone in the patient.

19. The method of claim 18, wherein placing the bone graft comprises mechanically bracing the implant in the segmental bone defect region.

20. The method of claim 18, wherein the bone graft is a bespoke bone graft shaped to fit the segmental bone defect region of the patient.

21. The method of claim 20, wherein the bone graft is shaped based on patient-specific imaging data.

22. The method of claim 18, wherein the graft core comprises demineralized bone matrix, fibrinogen, skin gelatin, and mesenchymal stem cells.

23. The method of claim 18, further comprising a step of placing the bone graft in an ectopic position in the patient in order to promote graft maturation and vascularization and to create a free or leashed flap prior to placement of the bone graft in the segmental bone defect region of the patient.

24. The bone graft of claim 1, wherein the pre-vascularized shell constituent comprises about 200,000 microvessels/ml isolated intact microvessel fragments.

* * * * *